(12) United States Patent
Machida et al.

(10) Patent No.: US 8,883,439 B2
(45) Date of Patent: Nov. 11, 2014

(54) BLOOD COMPONENT MEASUREMENT METHOD UTILIZING HEMOLYZED WHOLE BLOOD, AND KIT FOR THE METHOD

(75) Inventors: Reiko Machida, Takasaki (JP); Yayoi Irie, Takasaki (JP); Masahiko Yabuuchi, Takasaki (JP); Yoshihiko Umegae, Takasaki (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/054,992

(22) PCT Filed: Jul. 22, 2009

(86) PCT No.: PCT/JP2009/063077
§ 371 (c)(1),
(2), (4) Date: Mar. 24, 2011

(87) PCT Pub. No.: WO2010/010881
PCT Pub. Date: Jan. 28, 2010

(65) Prior Publication Data
US 2011/0165608 A1  Jul. 7, 2011

(30) Foreign Application Priority Data
Jul. 23, 2008 (JP) .................................. 2008-189870

(51) Int. Cl.
| | |
|---|---|
| *C12Q 1/28* | (2006.01) |
| *C12Q 1/26* | (2006.01) |
| *C12Q 1/00* | (2006.01) |
| *G01N 33/00* | (2006.01) |
| *G01N 33/72* | (2006.01) |
| *G01N 33/66* | (2006.01) |
| *G01N 33/70* | (2006.01) |
| *G01N 33/52* | (2006.01) |

(52) U.S. Cl.
CPC ................ *G01N 33/72* (2013.01); *G01N 33/52* (2013.01); *G01N 33/70* (2013.01); *G01N 33/66* (2013.01)
USPC .................................. 435/28; 435/4; 435/25

(58) Field of Classification Search
None
See application file for complete search history.

(56) References Cited

U.S. PATENT DOCUMENTS 4,810,640 A * 3/1989 Nakamura et al. ............... 435/25
6,309,852 B1 * 10/2001 Tazoe et al. ...................... 435/26

FOREIGN PATENT DOCUMENTS

| | | |
|---|---|---|
| JP | A-08-70893 | 3/1996 |
| JP | 10-062402 A | 3/1998 |
| JP | A-2003-521246 | 7/2003 |
| JP | 2004-535568 A | 11/2004 |
| WO | WO 01/57239 A2 | 8/2001 |
| WO | WO 02/097391 A2 | 12/2002 |
| WO | WO-A-03/005039 | 1/2003 |
| WO | WO-A-2008/072702 | 6/2008 |

OTHER PUBLICATIONS

Fukumara, Yukihito; et al; "Fully Enzymatic Method for Determining 1,5-Anhydro-D-glucitol in Serum." Clinical Chemistry, 40, 2013-2016, 1994.*
Kondo, Tamotsu; Tomizawa, Michiko; "Hemolysis by Nonionic Surface-Active Agents" Journal of Pharmaceutical Sciences, 57, 1246-12-48, 1968).*
Ohnishi, Massako; Sagitani, Hiromichi; "The Effect of Nonionic Surfactant Structure on Hemolysis" Journal of the American Oil Chemists' Society, 70, 679-684, 1993).*
European Search Report mailed Jul. 14, 2011 for the corresponding European patent application No. 09800395.7.
Kanai, Kanai's Manual of Clinical Laboratory Medicine (Thirtieth Edition), Section VII Clinical Chemical Test, Kanehara & Co., Ltd, Aug. 20, 1993.
International Search Report mailed Sep. 15, 2009 for the corresponding PCT application No. PCT/JP2009/063077.
Office Action mailed Jan. 4, 2013 for the related Japanese Patent Application No. 2010-542096.
Office Action mailed Feb. 4, 2014 for the corresponding Japanese Application No. 2010-521709.

* cited by examiner

*Primary Examiner* — Blaine Lankford
*Assistant Examiner* — David Berke-Schlessel
(74) *Attorney, Agent, or Firm* — Leason Ellis LLP.

(57) ABSTRACT

The invention is a method for determining the concentration of an analyte in whole blood, wherein the analyte is a component which is contained in the blood, is different from a component occurring only in a red blood cell, and can generate hydrogen peroxide upon the reaction with an oxidase. Whole blood is utilized in the method. The method comprises the steps of hemolyzing the whole blood and detecting hydrogen peroxide generated by the reaction between the analyte and the oxidase. The measurement method can avoid the inhibition of color development by hemoglobin and the interference with the measurement by hemoglobin. Further it can be used for biological tests that are carried out in a household, an individual doctor's clinic or at the bedside of patients without the need for any blood cell separation procedure or the like, because the measurement utilizes whole blood.

8 Claims, 3 Drawing Sheets

BLOOD COMPONENT MEASUREMENT METHOD UTILIZING HEMOLYZED WHOLE BLOOD, AND KIT FOR THE METHOD

CROSS-REFERENCE TO RELATED PATENT APPLICATIONS

This application is a U.S. National Phase Application under 35 U.S.C. §371 of International Patent Application No. PCT/JP2009/063077, filed Jul. 22, 2009, and claims the benefit of Japanese Patent Application No. 2008-189870, filed Jul. 23, 2008, all of which are incorporated by reference herein. The International Application was published in Japanese on Jan. 28, 2010 as International Publication No. WO/2010/010881 under PCT Article 21(2).

FIELD OF THE INVENTION

The present invention relates to a method for measuring a concentration of an analyte using whole blood without separating blood cells from the whole blood. The concentration is measured by detecting hydrogen peroxide which is generated from the reaction of an oxidase enzyme with the analyte in the hemolyzed whole blood obtained by mixing it with a hemolyzing agent. In addition, the present invention also relates to a method for converting the concentration of the analyte measured using whole blood to the concentration thereof measured using serum or plasma.

BACKGROUND OF THE INVENTION

Biochemical testing is essential for obtaining objective information used in diagnosing, treating, and preventing diseases. Typical test items include creatinine, uric acid, glucose, hemoglobin Ale, 1,5-anhydroglucitol, cholesterol, neutral fat, and phospholipid tests. Conventionally, most of these test items are measured by using serum or plasma (Non Patent Literature 1).

In these clinical chemical tests using serum or plasma, it is commonly known to use an oxidase specific for an analyte for determining the quantity of hydrogen peroxide generated in the oxidization thereof by the enzyme.

Hydrogen peroxide can also be detected by, for example, using peroxidase, catalase, a hydrogen peroxide electrode, or an oxygen electrode.

In a method using peroxidase, colorimetric detection, which utilizes a chromogen to determine the generated dye, is widely used because it provides a rapid and simple method.

However, even if serum or plasma is used, color development may be inhibited, or color detection may be interrupted due to a trace amount of hemoglobin produced by hemolysis occurring during the measuring operation.

For methods for measuring 1,5-anhydroglucitol as described in Patent Literature 1 and a package insert for 1,5-AG Kit for Animals (from Nippon Kayaku Co., Ltd.), 1,5-anhydroglucitol is measured using a treated solution obtained by adding purified water or a 10 mM EDTA aqueous solution to whole blood for hemolysis, centrifuging the hemolysate, and then passing the supernatant through a column. Thus, in this method, hemolyzed whole blood is not directly used without further processing.

Patent Literature 2 describes a method for measuring an analyte by a test strip using a hemolysate. However, this method is also not a method where hemolyzed whole blood is directly used without further processing.

PRIOR ART DOCUMENT

Patent Document

Patent Document 1: JP 08-70893 A
Patent Document 2: JP 2003-521246 A

Non Patent Document

Non Patent Document 1: Kanai's Manual of Clinical Laboratory Medicine (Thirtieth Edition), Section VII Clinical Chemical Test, Kanehara & Co., Ltd.

SUMMARY OF INVENTION

Technical Problem

The colorimetric determination of an analyte in blood using whole blood has been associated with the inhibition of color development or the interruption of calorimetric determination due to the presence of hemoglobin. Thus, it was necessary to use serum or plasma that is obtained by separating blood cells from whole blood. The blood cell separation before measuring an analyte in blood may be carried out at large facilities, such as general hospitals that have a large-scale testing site and/or an examination room with laboratory technicians, but it cannot be performed at a private clinic or home where no such testing facilities are available.

Accordingly, in order to perform the above biochemical testing at places such as a patient's home, private clinic, or the patient's bedside, there has been a need for a measuring method using whole blood without requiring a blood separation operation.

Solution to Problem

Through intensive studies for solving the above problems, the present inventors have discovered a method for detecting hydrogen peroxide generated by reacting an oxidase with an analyte in whole blood which has been hemolyzed. Further, the inventors also discovered a method for measuring the analyte in whole blood without separating blood cells from whole blood, by investigating an applicable chromogen to detect hydrogen peroxide and a preferable measuring wave length.

Thus, the present invention relates to:

(1) A method for measuring a concentration of an analyte using whole blood, where the analyte is a blood component that is different from components existing only in red blood cells and generates hydrogen peroxide when an oxidase is reacted therewith, the method comprising the steps of; hemolyzing whole blood, and detecting hydrogen peroxide generated by reacting the oxidase with the analyte;
(2) The measuring method according to item (1) above, wherein the step of hemolyzing whole blood comprises mixing the whole blood with a hemolyzing agent;
(3) The measuring method according to item (2) above, wherein the hemolyzing agent is a surfactant;
(4) The measuring method according to any one of items (1) to (3) above, wherein the step of detecting the hydrogen peroxide comprises using peroxidase and a chromogen to detect the color intensity of a dye generated from the chromogen;
(5) The measuring method according to item (4) above, wherein the chromogen is an oxidative coupling-coloring chromogen;

(6) The measuring method according to item (5) above, wherein the oxidative coupling-coloring chromogen is a chromogen comprising 4-aminoantipyrine, 3-methyl-2-benzothiazolinone hydrazone or 2-hydrazono-2,3-dihydro-3-methyl-6-benzothiazolesulfonic acid; and N-ethyl-N-sulfopropyl-3,5-dimethoxyaniline, 3-hydroxy-2,4,6-triiodobenzoic acid, N-ethyl-N-(2-hydroxy-3-sulfopropyl)-3-methoxyaniline, N-sulfopropylaniline, N-ethyl-N-sulfopropyl-m-anisidine or N-ethyl-N-sulfopropylaniline;

(7) The measuring method according to any one of items (4) to (6) above, wherein the detection of color intensity of the dye is carried out by measuring absorbance at a wavelength of 580 nm to 900 nm;

(8) The measuring method according to any one of items (1) to (7) above, wherein the analyte is creatinine, uric acid, glucose, 1,5-anhydroglucitol, cholesterol, neutral fat, or phospholipid;

(9) The measuring method according to any one of items (1) to (8) above, wherein the analyte is 1,5-anhydroglucitol;

(10) The measuring method according to item (9) above, wherein the oxidase is pyranose oxidase or L-sorbose oxidase;

(11) The measuring method according to any one of items (1) to (10) above, further comprising the step of eliminating a component that would interfere with the measurement of the analyte before detecting the hydrogen peroxide;

(12) A measurement kit used for the method according to any one of items (1) to (11) above, comprising a reagent for hemolyzing whole blood and a reagent for detecting hydrogen peroxide;

(13) The measurement kit according to item (12) above, wherein the reagent for hemolyzing whole blood is a hemolyzing agent and the reagents for detecting hydrogen peroxide are peroxidase and a chromogen;

(14) The measurement kit according to item (13) above, wherein the hemolyzing agent is a surfactant and the chromogen is an oxidative coupling-coloring chromogen;

(15) The measurement kit according to item (14) above, wherein the oxidative coupling-coloring chromogen is selected from a group consisting of a chromogen comprising 4-aminoantipyrine, 3-methyl-2-benzothiazolinone hydrazone or 2-hydrazono-2,3-dihydro-3-methyl-6-benzothiazolesulfonic acid; and N-ethyl-N-sulfopropyl-3,5-dimethoxyaniline, 3-hydroxy-2,4,6-triiodobenzoic acid, N-ethyl-N-(2-hydroxy-3-sulfopropyl)-3-methoxyaniline, N-sulfopropylaniline, N-ethyl-N-sulfopropyl-m-anisidine or N-ethyl-N-sulfopropylaniline;

(16) The measurement kit according to any one of items (12) to (15) above, further comprising an oxidase for the analyte;

(17) The measurement kit according to any one of items (12) to (16) above, wherein the analyte is 1,5-anhydroglucitol;

(18) The measurement kit according to item (16) or (17) above, wherein the oxidase is pyranose oxidase or L-sorbose oxidase;

(19) A method for converting the concentration of the analyte in whole blood into a concentration of the analyte in serum or plasma, the conversation being done by dividing the concentration of the analyte determined by the method according to any one of items (1) to (11) above using whole blood by an average of the whole blood measurement recovery rates which represent ratios between the analyte concentration obtained in advance by the measuring method according to any one of items (1) to (11) above and the analyte concentration obtained by using serum or plasma;

(20) A method for converting the concentration of an analyte in whole blood into a concentration of the analyte in serum or plasma, the conversion being done by measuring a numerical value related to a hemoglobin concentration in a sample in which whole blood is hemolyzed, and by dividing the concentration of the analyte determined by the method according to any one of items (1) to (11) above using whole blood by a whole blood measurement recovery rate obtained through a function equation using the numerical value; and

(21) The conversion method according to item (20), wherein the numerical value related to the hemoglobin concentration in a sample is an absorbance.

Advantageous Effects of Invention

According to the measuring method of the present invention, it is possible to measure the concentration of a blood component, for example, 1,5-anhydroglucitol, conveniently, rapidly and accurately at patient's home, private clinic or patient's bedside where no blood cell separation device is available, because whole blood can be used without separating blood cells for the measurement of the analyte concentration, in which the quantity of hydrogen peroxide generated by the reaction of an oxidase enzyme with the analyte is determined.

DESCRIPTION OF EMBODIMENTS

Figure 1:
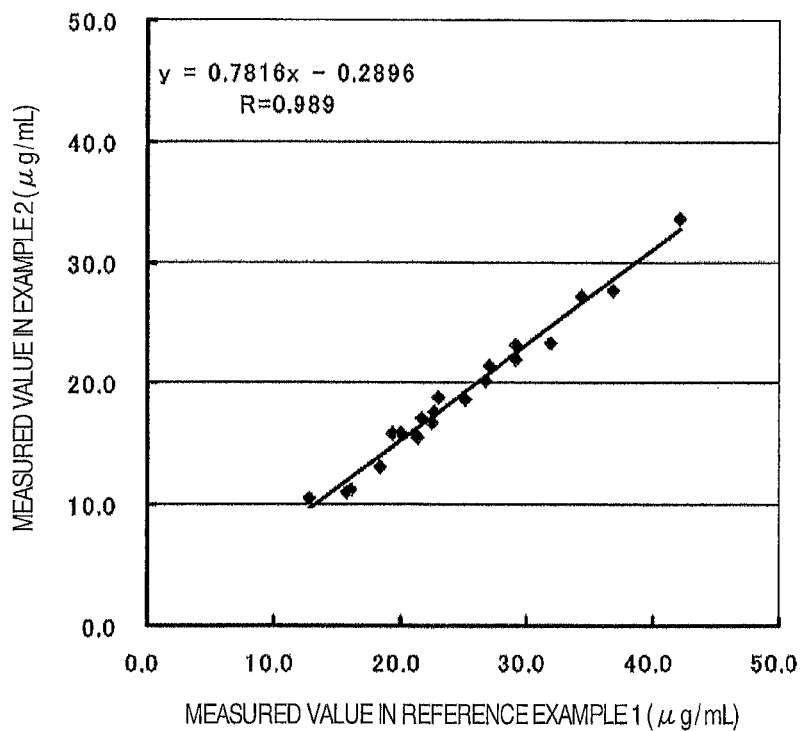
FIG. 1 is a graph showing the correlation between the measured values obtained by a conventional method for measuring a plasma sample (Reference Example 1) and in Example 2 in which a whole blood sample was hemolyzed before measurement.

The present invention is a method for measuring a concentration of an analyte using whole blood, where the analyte is a blood component that is different from components existing only in red blood cells and generates hydrogen peroxide when an oxidase is reacted therewith, the method comprising the steps of: hemolyzing whole blood and detecting hydrogen peroxide generated by reacting the oxidase with the analyte.

The whole blood to which the method of the present invention is applied is the blood used under the as-collected condition without separating blood cells. The whole blood may contain an anticoagulant and a glycolytic inhibitor, such as dipotassium ethylenediamine tetraacetate (EDTA.2K), disodium ethylenediamine tetraacetate (EDTA.2Na), heparin, sodium fluoride, sodium citrate, and monoiodoacetic acid, all of which are additives found in a blood-correcting vessel. When a blood sample is stored, it is preferable to use the sample collected using a blood-collecting vessel containing sodium fluoride and heparin.

The whole blood may also be collected with a lancet device or the like used for self monitoring of blood glucose without using a blood-collecting vessel or the like. The site for blood collection by lancet is not particularly limited. Examples thereof include the outer forearm, the abdominal wall, or the upper outer arm in addition to the finger tip. The volume of collected blood is, for example, 200 μL or less, preferably of the order of 0.1 μL to 50 μL, more preferably of the order of 3 μL to 20 μL.

The analyte to which the present invention is applied is a blood component that is different from components existing only in red blood cells and a substance generating hydrogen peroxide on reaction with an oxidase. Non-limiting examples thereof include creatinine, uric acid, glucose, 1,5-anhydroglucitol, cholesterol, neutral fat, and phospholipid. Among others, 1,5-anhydroglucitol is preferable.

The components existing only in red blood cells include, for example, hemoglobin Alc and hemoglobin.

The step of hemolyzing whole blood in the measuring method of the present invention means a step of lysing blood cells, that is, rupturing the cell membrane. For example, the step may comprise the processes of mixing a hemolyzing agent such as a surfactant-containing solution, a solution of a saponin or a hypotonic solution, or physical treatment such as freezing and thawing, ultrasonication or pressure treatment. Among the above processes, the step of mixing of a hemolyzing agent containing a surfactant with whole blood is preferable.

The surfactant is not particularly limited provided that it can hemolyze blood without affecting the measurement of the analyte. Examples thereof include surfactants such as an anionic surfactant, a cationic surfactant, an amphoteric surfactant, and a nonionic surfactant. Among those, a nonionic surfactant is preferable.

Examples of the nonionic surfactant include a polyoxyethylene surfactant, a sorbitan fatty acid ester surfactant, and a glycerin fatty acid ester surfactant. Among those, a polyoxyethylene surfactant is preferable.

Examples of the polyoxyethylene surfactant include a polyoxyethylene alkyl phenyl ether and a polyoxyethylene sorbitan fatty acid ester. Among those, a polyoxyethylene alkyl phenyl ether is preferable.

The alkyl group in the polyoxyethylene alkyl phenyl ether is preferably a (C7 to C10) alkyl group such as an octyl group or a nonyl group; examples thereof include Nonion HS210 (from NOF Corporation), Triton X-100 (from Wako Pure Chemical Industries Ltd.), Triton X-405 (from Wako Pure Chemical Industries Ltd.), and Emulgen 920 (from Kao Corporation).

The concentration of the surfactant in the hemolyzing agent is of the order of 0.0001% by weight to 10% by weight, preferably of the order of 0.01% by weight to 2% by weight.

The oxidase for an analyte in the measuring method of the present invention is not particularly limited provided that it has the ability to oxidize the analyte and produces hydrogen peroxide by oxidation reaction; a known oxidase may be used.

Examples of the oxidase include glucose oxidase for measurement of glucose, uric acid oxidase for measurement of uric acid, cholesterol oxidase for measurement of cholesterol, and pyranose oxidase or L-sorbose oxidase for measurement of 1,5-anhydroglucitol.

Examples of the pyranose oxidase or L-sorbose oxidase include; pyranose oxidase derived from Basidiomycetous fungi No. 52 (deposited under Accession Number FERM BP10106 in International Patent Organism Depositary, National Institute of Advanced Industrial Science and Technology) described in JP 05-304997 A, pyranose oxidase derived from *Polyporus* obtusus ATCC26733 described in JP-63-185397 A, L-sorbose oxidase derived from *Trametes sanguinea* IFO4923, and an enzyme derived from microorganism such as *Escherichia coli* transfected with the gene which is identified to have pyranose oxidase or L-sorbose oxidase activity and which is suitably modified through conventional genetic engineering techniques.

Particularly preferred examples thereof include pyranose oxidase derived from Basidiomycetous fungi No. 52.

According to the measuring method of the present invention, the concentration of an oxidase during measurement is of the order of 1 KU/L to 200 KU/L, preferably of the order of 20 KU/L to 100 KU/L. In this respect, 1 U is the amount of enzyme producing 1 mmole/minute of hydrogen peroxide in an enzymatic reaction using a substrate for the enzyme at 37° C.

According to the measuring method of the present invention, the step of detecting hydrogen peroxide generated by the reaction of an oxidase enzyme with the analyte is preferably a step of measuring color intensity of a dye produced by reacting peroxidase and a chromogen. A chromogen that produces a dye having an absorption in the wavelength of 560 nm to 900 nm is is preferable. A more preferable chromogen is the one that generates a dye having a molecular absorption coefficient of 10,000 or more in the wavelength from 560 nm to 900 nm. Examples of the chromogen include an oxidative coloring chromogen or an oxidative coupling-coloring chromogen. An oxidative coupling-coloring chromogen is preferable.

Examples of the oxidative coloring chromogen include N-(carboxymethylaminocarbonyl)-4,4'-bis(dimethylamino) diphenylamine sodium salt (DA64), 10-carboxymethylaminocarbonyl-3,7-bis(dimethylamino)phenothiazine sodium salt (DA67), Bis[3-bis(4-chlorophenyl)methyl-4-dimethylaminophenyl]amine (BCMA), Bis[3-bis(4-chlorophenyl) methyl-4-carboxyethylaminophenyl]amine, 10-N-methylcarbamoyl-3,7-dimethylamino-10H-phenothiazine (MCDP), 10-N-carboxymethylcarbamoyl-3,7-dimethylamino-10H-phenothiazine (CCAP), 3,3',5,5'-tetramethylbenzidine (TMBZ), and N,N,N',N',N'',N''-hexa(3-sulfopropyl)-4,4',4''-triaminotriphenylmethane hexasodium salt (TPM-PS).

The oxidative coupling-coloring chromogen consists of two types of compounds which are oxidatively coupled in the presence of hydrogen peroxide and peroxidase to generate a dye. Examples of the combination of the two types of compounds include a combination of a coupler and aniline or its derivative (Trinder's reagent) and a combination of a coupler and phenol or its derivative.

Examples of the coupler include; 4-aminoantipyrine (4AAP), 3-methyl-2-benzothiazolinonehydrazone (MBTH), 2-hydrazono-2,3-dihydro-3-methyl-6-benzothiazolesulfonic acid (SMBTH), N-methyl-3-methoxy-4'-amino-diphenylamine (NCP-06), and N-methyl-4-amino-diphenylamine (NCP-04).

Examples of the aniline derivatives (Trinder's reagent) or the phenol derivatives capable of being oxidatively condensed with the coupler include; N-ethyl-N-(3-methylphenyl)-N'-succinylethylene diamine (EMSE), N-ethyl-N-(2-hydroxy-3-sulfopropyl)-3-methylaniline (TOOS), N-ethyl-N-sulfopropyl-3,5-dimethoxyaniline (DAPS), N-sulfopropylaniline (HALPS), N-ethyl-N-sulfopropyl-m-anisidine (ADPS), N-ethyl-N-sulfopropylaniline (ALPS), N-sulfopropyl-3,5-dimethoxyaniline (HDAPS), N-ethyl-N- sulfopropylaniline (ALPS), N-sulfopropyl-3,5-dimethylaniline (MAPS), and 3-hydroxy-2,4,6-triiodobenzoic acid (HTIB).

Among these, oxidative coupling-coloring chromogens as preferable chromogens include, for example, 4AAP, MBTH, or SMBTH as the coupler, and DAPS, HTIB, TOOS, HALPS, ADPS, or ALPS as the aniline derivative (Trinder's reagent) or the phenol derivative that are condensed with these couplers. Particularly preferred examples thereof include SMBTH and DAPS, SMBTH and HTIB, SMBTH and TOOS, SMBTH and HALPS, SMBTH and ADPS, SMBTH and ALPS, and 4AAP and ALPS.

According to the measuring method of the present invention, the working concentration of the chromogen during measurement is 0.1 mM to 100 mM, preferably 1 mM to 50 mM. The pH during measurement is 5.5 to 9.5, preferably 6.0 to 8.0.

According to the measuring method of the present invention, when detecting the absorbance of a dye generated from the chromogen, one may use a spectrophotometer. The measurement wavelength therefor is preferably from 580 to 900 nm, particularly preferably from 600 to 800 nm because it is less affected by hemoglobin whose absorption peaks are around 540 nm and 575 nm.

According to the measuring method of the present invention, the step of eliminating a component interfering with the measurement of the analyte may be carried out before the step of detecting hydrogen peroxide, which is generated by the reaction of an oxidase enzyme with the analyte. The elimination of a component interfering with the measurement comprises a pretreatment step in which the interfering component is converted to a substance that does not react with the oxidase for the analyte.

As an example of the measuring methods of the present invention, a measurement procedure using an automated analyzer, which is actually used for biological examination, is described below.

Examples of the automated analyzer include; Automated Analyzer Model 7150, Automated Analyzer Model 7020 and Automated Analyzer Model 9000 from Hitachi High-Technologies Corporation and an automated analyzer, BioMajesty, from JEOL Ltd.

The measurement is performed by setting whole blood to be measured in a sample port of an automated analyzer; by setting a first reagent solution containing a reagent used in the step of hemolyzing the whole blood; by setting a second reagent solution containing a reagent used in the step of detecting hydrogen peroxide generated by the reaction of an oxidase enzyme with an analyte; by inputting the dispensation amount of the sample, the first reagent solution, and the second reagent solution into cuvettes of the analyzer; and by setting the reaction time, reaction temperature and measurement wavelength to the analyzer.

The first reaction reagent may also contain a pretreatment reagent for eliminating a component interfering with the measurement of an analyte, e.g., ascorbic acid oxidase (ASOD) for preventing the inhibition of color development due to ascorbic acid or uric acid oxidase for preventing the inhibition of color development due to uric acid, in addition to the reagent used in the step of hemolyzing the whole blood. Particularly, when 1,5-anhydroglucitol is measured using pyranose oxidase (PROD), a reagent for eliminating glucose, galactose, and the like is preferably added to the first reaction reagent as shown in examples described in this specification because pyranose oxidase also reacts with saccharides other than 1,5-anhydroglucitol in blood. As a method for converting glucose to a substance not reacting with pyranose oxidase, one may use the following methods including; the oxidation of glucose by glucose oxidase as described in Japanese Patent No. 2983015, and the phosphorylation thereof by hexokinase or glucokinase, the oxidation of glucose by glucose oxidase or glucose dehydrogenase as described in JP 2001-78797 A, and the conversion thereof to fructose-1,6-diphasphoric acid by hexokinase, phosphohexose isomerase and 6-phosphofructokinase, or glucose isomerase, fructokinase and 6-phosphofructokinase as described in Japanese Patent Nos. 3170320 and 3217180.

When employing an oxidative coupling-coloring chromogen, which is the combination of the coupler and the aniline derivative (Trinder's reagent) or the phenol derivative, to detect hydrogen peroxide, it is preferable that each component be added separately to the first reaction reagent and the second reaction reagent; the oxidase for an analyte is preferably added to the second reaction reagent. When employing peroxidase or a leuco dye for detecting hydrogen peroxide, it is possible to add them to either the first reaction reagent or the second reaction reagent. However, when both peroxidase and the leuco dye are used, it is preferably that each of them be added separately to the first reaction reagent and the second reaction reagent.

The first reaction reagent and the second reaction reagent also preferably have a pH of 6 to 10, and 2-[4-(2-hydroxyethyl)-1-piperazinyl]propanesulfonic acid (HEPES), 2-morpholinoethanesulfonic acid (MES) or the like is preferably used therein as a buffering agent.

In addition, it is preferable to add a protein (e.g., bovine serum albumin), a saccharide (e.g., trehalose) and metal salts (e.g., potassium chloride and magnesium chloride) for stabilizing enzymes, sodium chloride for adjusting the salt concentration, and a chelating agent (e.g., EDTA•2Na or EDTA•2K) for preventing the inhibition of color development due to heavy metal ion contamination.

The sample amount may be of the order of 1 µL to 40 µL, preferably of the order of 2 µL to 10 µL. For the sample amount of such order, the first reaction reagent is used in an amount of the order of 50 µL to 500 µL, preferably of the order of 50 µL to 300 µL, and the second reaction reagent is used in an amount of the order of 50 µL to 500 µL, preferably of the order of 50 µL to 250 µL. The mixing volume ratio of the sample and the first reaction reagent is 1:9 to 1:500, preferably 1:20 to 1:200, more preferably 1:20 to 1:140. The percentage of the sample volume to the total volume in the reaction vessel in the second reaction is of the order of 0.5% to 10%, preferably of the order of 1% to 5%.

The reaction time for the reaction of the sample and the first reaction reagent is preferably 5 minutes and the time for the subsequent reaction when the second reaction reagent is added after the first reaction is preferably 5 minutes.

The reaction temperature is 20° C. to 37° C., preferably 37° C.

The measurement wavelength is in the range of 580 to 900 rim and may be selected according to the absorption wavelength of the color from a dye produced for the detection of hydrogen peroxide.

As another embodiment of the measuring method of the present invention, there is a method for sequentially mixing whole blood with a solution containing a hemolyzing agent, a solution containing an oxidase for an analyte, and a solution containing a reagent used in the step of detecting hydrogen peroxide generated by the oxidase in a cuvette of a spectrophotometer, and then measuring the absorbance of the mixture.

As still another embodiment, there is a method for sequentially mixing whole blood with a dry agent containing a hemolyzing agent, a solution containing an oxidase used against an analyte, and a solution containing a reagent used in the step of detecting hydrogen peroxide generated by the oxide in a cuvette of a spectrophotometer and measuring the absorbance of the mixture.

The present invention also contains a kit for measuring an analyte, comprising a reagent for hemolyzing whole blood and a reagent for detecting hydrogen peroxide. The measurement kit may comprise a dry reagent for hemolyzing whole blood, a solution for reconstituting the dry reagent, a dry reagent for detecting hydrogen peroxide, and a solution for reconstituting the latter dry reagent. One of the reagents may also comprise a dry reagent and a reconstitution solution, while the other being a liquid reagent.

The constitution of the measurement kit of the present invention may be divided into two parts or more.

Examples of the reagent for hemolyzing whole blood include the above hemolyzing agents. In particular, the surfactant is preferable.

Examples of the reagent for detecting hydrogen peroxide include the above-described peroxidase and chromogens. In particular, the oxidative coupling-coloring chromogen is preferable. Examples of the oxidative coupling-coloring chromogen include the above-described examples. In particular, a preferable combination thereof is also the same as that described above.

In addition, the kit for measuring an analyte according to the present invention may also contain an oxidase for the analyte. Examples of the oxidase include the above-described oxidases.

The analyte for the measurement kit of the present invention is preferably 1,5-anhydroglucitol, and examples of the oxidase include the above-described pyranose oxidase or L-sorbose oxidase.

The present invention also encompasses a method for converting a measured value of the analyte determined by the above-described measuring method using whole blood to the concentration of the analyte in serum or plasma. The concentration of the analyte in serum or plasma is a value obtained when the analyte in serum or plasma prepared by separating blood cells from whole blood is measured by a conventional method. The concentration of an analyte in serum or plasma determined by a conventional method is actually used in clinical sites for the diagnosis and follow-up of disease, the evaluation of a therapeutic effect, or the like, and its clinical importance has already been established. Thus, the conversion method of the present invention is useful.

The conversion method of the present invention comprises the steps of: pre-determining an average of the whole blood measurement recovery rates, that represent the ratios between the measured values of an analyte determined by the measuring method of the present invention using whole blood and the measured values of the analyte obtained using the serum or plasma prepared by separating blood cells from whole blood, obtained from the same samples while using many samples; dividing the measured value of the analyte newly measured by the method of the present invention using whole blood by the average of the whole blood measurement recovery rates; and determining the concentration of the analyte in serum or plasma.

This method is more useful when the measured value in hemolyzed whole blood is not affected by blood cell components and the individual variations are small in the influence of blood cells on the measured value.

The conversion method of the present invention also encompasses a method for calculating the concentration of the analyte in serum or plasma by dividing the measured value of the analyte in whole blood, which is determined with the method of the present invention, by a recovery rate, which is the value calculated from a correlation formula for the recovery rates obtained from the sample sets and measured values related to the hemoglobin concentrations. For example, the absorbances (mABS×10) at the 24th point in measuring the whole blood samples, that is, the absorbances before addition of the R2 reagent, were found to show good correlation with the recovery rates for whole blood measurement (a/b) (correlation coefficient R: 0.67). From this, the following correlation formula as a linear approximation formula is derived:

Recovery rate for whole blood measurement (a/b; %)=−0.0127×(Absorbance at the 24th point; mABS×10)+125.65.

The correlation formula is not particularly limited provided that it has a high correlation coefficient. However, preferred examples thereof include a linear approximation formula, a power approximation formula, a logarithmic approximation formula, and the like. Particularly, if an accurate correlation formula is prepared in advance by using many samples, more accurate conversion can be carried out.

The present method can particularly correct the influence of an amount of blood cell components that may vary among individuals, or the affect derived from blood cell components in a hemolysate on the measurement, enabling more accurate conversion. In addition, the conversion method of the present invention has potential to be able to correct the difference between lots of the reagent used for measurement of an analyte.

The measured value related to the hemoglobin concentration is not particularly limited provided that it can reflect the relative hemoglobin concentration between samples. However, the absorbance of the sample, namely, the absorbance of the hemolysate obtained by adding the first reagent solution containing a hemolyzing agent to a whole blood sample is preferable. In this case, the absorbance may be measured at the absorption wavelength of any part of the absorption spectrum of hemoglobin and does not necessarily need to be measured at the absorption peak wavelength.

For example, in the case of measurement using the above automated analyzer or the like, if the measurement wavelength for detecting hydrogen peroxide is on the shoulder of the absorption spectrum of hemoglobin, the measurement can be carried out at the wavelength. Also, if the wavelength at the shoulder of the absorption spectrum of hemoglobin is set as a subwavelength for canceling the influence of the inherent absorption of a sample, i.e., the sample blank, the absorbance can be most reasonably measured as a numerical value related to the hemoglobin concentration.

The present invention is described in further detail with reference to the following Examples, Reference Examples and Comparative Examples. However, this invention is not intended to be limited to these Examples. Each of constituents of "R1 Reagent" and "R2 Reagent" is described below with the concentration thereof in each reagent. In addition, the enzyme amount of 1 U is determined by a method known to the public through publication. For example, 1 U of pyranose oxidase (PROD) is the amount of enzyme using 1,5-anhydroglucitol as a substrate to reduce 1 mole of WST-1 for one minute at 37° C.

Example 1

Measurement of 1,5-Anhydroglucitol in Whole Blood Sample by Measuring Method of the Present Invention 1,5-Anhydroglucitol (1,5-AG)-measuring reagents (a first reaction reagent (R1 reagent) and a second reaction reagent (R2 reagent)) with the following compositions, containing a surfactant as a hemolyzing agent were prepared to measure the 1,5-AG concentration in 21 of whole blood samples from 21 subjects using Automated Analyzer Model 7150 (from Hitachi High-Technologies Corporation).

| R1 Reagent (Pretreatment Solution: pH 7.5): | |
|---|---|
| 4-(2-Hydroxyethyl)-1-piperadineethanesulfonic acid (HEPES) | 50 mM |
| Nonion HS210 | 0.5% |
| KCl | 50 mM |
| NaCl | 100 mM |
| $MgCl_2 \cdot 6H_2O$ | 7.5 mM |
| $NaN_3$ | 0.1% |
| EDTA•2Na | 0.1 mM |
| Phosphoenolpyruvic acid (PEP) | 2 mM |
| Adenosine-5'-triphosphate (ATP) | 1 mM |
| Pyruvate kinase (PK) | 1 KU/L |
| Glucokinase (GK) | 1 KU/L |
| Ascorbate oxidase (ASOD) | 2 KU/L |
| SMBTH | 1.5 mM |
| R2 Reagent (Color Development Solution: pH 7.5): | |
| HEPES | 50 mM |
| NaCl | 100 mM |
| $NaN_3$ | 0.1% |
| EDTA•2Na | 0.5 mM |
| Horseradish peroxidase (HRP) | 5 KU/L |
| Pyranose oxidase (PROD) | 80 KU/L |
| DAPS | 6 mM |

HS210: Nonionic surfactant (from NOF Corporation)
HEPES, EDTA•2Na, SMBTH, and DAPS: from Dojindo Laboratories
KCl, NaCl, $MgCl_2 \cdot 6H_2O$, and $NaN_3$: from Wako Pure Chemical Industries Ltd.
PEP and ATP: from Oriental Yeast Co., Ltd.
PK, ASOD, and HRP: from Toyobo Co., Ltd.
GK: from Unitika Ltd.
PROD: Derived from Basidiomycetous fungi No. 52

Using the above-mentioned reagents, the 1,5-AG concentrations in 21 whole blood samples were measured with the following parameters employing Automated Analyzer Model 7150, and the results are shown in Table 1.

| Measurement Parameters: | |
|---|---|
| Analysis method | 2 Point end |
| Measurement points | 24 to 50 |
| Sample amount | 2 μL |
| R1 reagent | 280 μL |
| R2 reagent | 140 μL |
| Temperature | 37° C. |
| Measurement wavelength (main) | 750 nm |
| Calibration method | Straight-line method |
| Reference standard (1) | Saline (blank solution) |
| Reference standard (2) | 1,5-AG (50 μg/mL) saline solution |

Reference Example 1

Measurement of 1,5-AG in Plasma Sample after Centrifugation of Whole Blood by Conventional Method Twenty-one whole blood samples, which were the same whole blood samples as the whole blood samples measured in Example 1, were each centrifuged at 3,000 rpm for 5 minutes, and the supernatants were quantitatively measured with the following parameters using the conventional reagents for measuring 1,5-anhydro-D-glucitol (Lana 1,5-AG Auto Liquid; from Nippon Kayaku Co., Ltd.) and Automated Analyzer Model 7150. The results are shown in Table 1.

| Measurement Parameters: | |
|---|---|
| Analysis method | 2 Point end |
| Measurement points | 24 to 50 |
| Sample amount | 8 μL |
| R1 Reagent of Lana 1,5-AG Auto Liquid | 240 μL |
| R2 Reagent of Lana 1,5-AG Auto Liquid | 120 μL |
| Temperature | 37° C. |
| Measurement wavelength (sub/main) | 700/546 nm |
| Calibration method | Straight-line method |
| Reference standard (1) | Saline (blank solution) |
| Reference standard (2) | 1,5-AG (50 μg/mL) saline solution |

Reference Example 2

Measurement of 1,5-AG in Plasma Sample after Centrifugation of Whole Blood by the Same Method as That in Example 1

The same 21 samples of whole blood samples as those measured in Example 1 were each centrifuged at 3,000 rpm for 5 minutes and then the supernatants were quantitatively measured for 1,5-AG with the same parameters using the same reagents as those in Example 1. The results are shown in Table 1.

Comparative Example 1

Measurement of 1,5-AG in Whole Blood Sample Not Subjected to Hemolysis Treatment Twenty-one samples of the same whole blood samples as the whole blood samples measured in Example 1 were each quantitatively measured for 1,5-AG with the same parameters as those in Reference Example 1 using the same reagents for measuring 1,5-anhydro-D-glucitol (Lana 1,5-AG Auto Liquid; from Nippon Kayaku Co., Ltd.) and Automated Analyzer Model 7150. The results are shown in Table 1.

TABLE 1

Measured Value of 1,5-AG (Unit: μg/mL)

| Sample | Reference Example 1 Lana 1,5-AG Auto Liquid Plasma | Example 1 Reagent in Example 1 Whole Blood | Reference Example 2 Reagent in Example 1 Plasma | Comparative Example 1 Lana 1,5-AG Auto Liquid Whole Blood |
|---|---|---|---|---|
| 1 | 18.4 | 12.2 | 18.4 | 15.1 |
| 2 | 25.0 | 19.4 | 26.1 | 40.8 |
| 3 | 22.6 | 16.8 | 25.1 | 25.2 |
| 4 | 36.9 | 26.9 | 38.6 | 7.4 |
| 5 | 15.8 | 10.1 | 18.4 | 10.2 |
| 6 | 26.8 | 18.5 | 29.7 | 20.4 |
| 7 | 32.0 | 22.9 | 35.1 | 85.0 |
| 8 | 19.4 | 18.3 | 21.4 | 17.4 |
| 9 | 29.1 | 24.3 | 30.7 | 28.4 |
| 10 | 21.7 | 14.1 | 24.1 | 12.8 |
| 11 | 34.4 | 25.7 | 35.4 | 34.4 |
| 12 | 42.1 | 31.1 | 41.4 | −0.6 |
| 13 | 12.8 | 11.4 | 14.4 | 7.8 |
| 14 | 27.0 | 21.3 | 29.2 | 9.0 |
| 15 | 20.0 | 14.8 | 21.0 | 12.8 |
| 16 | 29.2 | 21.2 | 31.5 | 5.4 |
| 17 | 21.3 | 13.4 | 28.9 | 67.1 |
| 18 | 22.9 | 16.3 | 25.9 | 50.0 |
| 19 | 19.3 | 15.5 | 22.0 | 9.0 |

TABLE 1-continued

Measured Value of 1,5-AG (Unit: μg/mL)

| Sample | Reference Example 1 Lana 1,5-AG Auto Liquid Plasma | Example 1 Reagent in Example 1 Whole Blood | Reference Example 2 Reagent Reagent in Example 1 Plasma | Comparative Example 1 Lana 1,5-AG Auto Liquid Whole Blood |
|---|---|---|---|---|
| 20 | 16.1 | 9.6 | 17.2 | 8.3 |
| 21 | 22.5 | 14.6 | 25.5 | 16.6 |

From the result in Table 1, the correlation coefficient R between the measured values in Reference Example 1 and Comparative Example 1 was found to be 0.106. This result indicates that 1,5-AG in a whole blood sample cannot be measured by the reagents and method of Comparative Example 1. On the other hand, the correlation coefficient R between the measured values in Reference Example 1 and Reference Example 2 was found to be 0.976. This result indicates that 1,5-AG in a plasma sample can be measured using the reagent containing a hemolyzing agent. The correlation coefficient R between the measured values in Reference Example 1 and Example 1 was found to be 0.957, indicating that 1,5-AG in a whole blood sample can be measured using a reagent containing a hemolyzing agent.

The present invention has enabled the accurate measurement of the 1,5-AG concentration using a whole blood sample by the colorimetric method.

Example 2 and Comparative Example 2

Comparison of Presence and Absence of Hemolyzing Agent

R1 reagents containing 0% (Comparative Example 2) and 0.5% (Example 2) of a surfactant, HS210, as the hemolyzing agent were each prepared to determine the quantity of 1,5-AG in 21 samples of the same whole blood samples as those in Example 1 with the following parameters using Automated Analyzer Model 7150. In Example 2, the first reaction which is the reaction of each sample and an R1 reagent is a step comprising hemolysis. On the other hand, in Comparative Example 2, hemolysis does not take place because no hemolyzing agent is contained.

Figure 2:
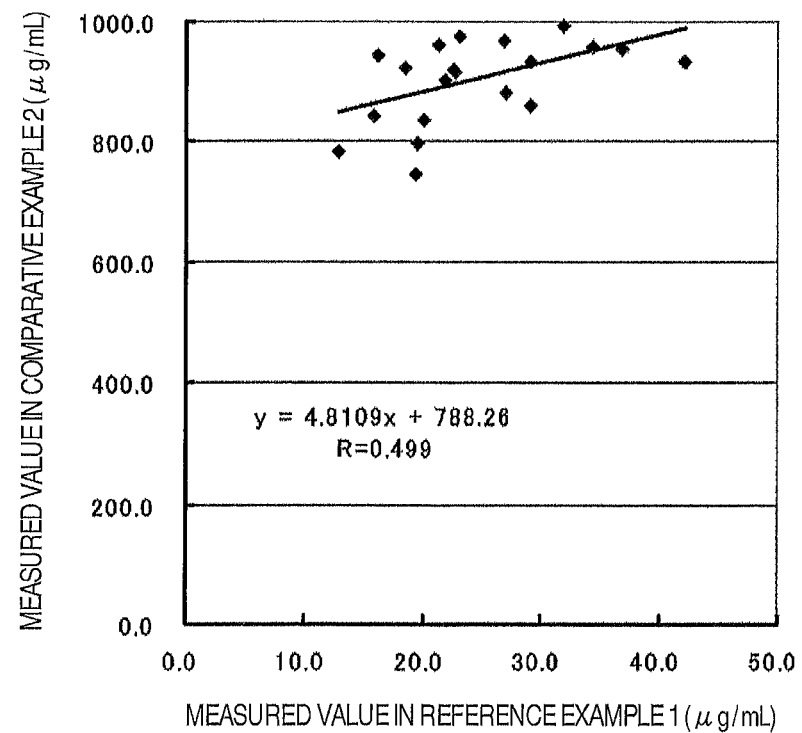
FIG. 2 is a graph showing the correlation between the measured values obtained by a conventional method for measuring a plasma sample (Reference Example 1) and in Comparative Example 2 in which a whole blood sample was not hemolyzed before measurement.

For each sample, the measured values in Example 2 or Comparative Example 2 against the measured values in Reference Example 1 were plotted and the charts are shown in FIG. 1 or FIG. 2.

Measuring Reagents in Example 2

| R1 Reagent (Pretreatment Solution: pH 7.5): | |
|---|---|
| HEPES | 50 mM |
| Nonion HS210 | 0.5% |
| KCl | 50 mM |
| NaCl | 100 mM |
| MgCl$_2$•6H$_2$O | 7.5 mM |
| NaN$_3$ | 0.1% |
| EDTA•2Na | 0.1 mM |
| PEP | 2 mM |
| ATP | 1 mM |
| PK | 1 KU/L |
| GK | 1 KU/L |
| ASOD | 2 KU/L |
| DAPS | 3 mM |

| R2 Reagent (Color Development Solution: pH 7.5): | |
|---|---|
| HEPES | 50 mM |
| NaCl | 100 mM |
| NaN$_3$ | 0.1% |
| EDTA•2Na | 0.5 mM |
| HRP | 5 KU/L |
| PROD | 80 KU/L |
| SMBTH | 3 mM |

Measuring Reagents in Comparative Example 2

| R1 Reagent (Pretreatment Solution: pH 7.5): | |
|---|---|
| HEPES | 50 mM |
| Nonion HS210 | 0.0% |
| KCl | 50 mM |
| NaCl | 100 mM |
| MgCl$_2$•6H$_2$O | 7.5 mM |
| NaN$_3$ | 0.1% |
| EDTA•2Na | 0.1 mM |
| PEP | 2 mM |
| ATP | 1 mM |
| PK | 1 KU/L |
| GK | 1 KU/L |
| ASOD | 2 KU/L |
| DAPS | 3 mM |

| R2 Reagent (Color Development Solution: pH 7.5): | |
|---|---|
| HEPES | 50 mM |
| NaCl | 100 mM |
| NaN$_3$ | 0.1% |
| EDTA•2Na | 0.5 mM |
| HRP | 5 KU/L |
| PROD | 80 KU/L |
| SMBTH | 3 mM |

Measurement Parameters in Example 2 and Comparative Example 2

| Analysis method | 2 Point end |
|---|---|
| Measurement points | 24 to 50 |
| Sample amount | 7 μL |
| R1 reagent | 240 μL |
| R2 reagent | 120 μL |
| Temperature | 37° C. |
| Measurement wavelength (main) | 750 nm |
| Calibration method | Straight-line method |
| Reference standard (1) | Saline (blank solution) |
| Reference standard (2) | 1,5-AG (50 μg/mL) saline solution |

As shown in FIG. 1, the correlation coefficient R between the measured values in Example 2, in which whole blood samples were hemolyzed with the R1 reagent containing the hemolyzing agent, and Reference Example 1 was found to be 0.989, indicating good correlation. On the other hand, as shown in FIG. 2, the correlation coefficient R between the measured values in Comparative Example 2, in which whole blood samples were not hemolyzed with the R1 reagents not containing hemolyzing agent, and Reference Example 1 was found to be 0.499, demonstrating that no correlation existed therebetween and 1,5-AG could not be measured with Comparative Example 2.

These results indicate that the hemolysis of whole blood is advantageous for measurement of an analyte in whole blood.

Examples 3 to 6

Measurement of 1,5-AG Using Various Chromogens for Oxidative Coupling-Coloring Chromogens SMBTH-HTIB (Example 3), SMBTH-HALPS (Example 4), SMBTH-ADPS (Example 5) or 4AAP-ALPS (Example 6) was used as an oxidative coupling-coloring chromogen to determine the quantity of 1,5-AG in 21 samples of the same whole blood samples as those in Example 1 with the following parameters employing Automated Analyzer Model 7150. The correlation coefficients of the measured values of Examples 3-6 with the measured values of in Reference Example 1 are shown in Table 2.

Measurement Reagents in Example 3

| R1 Reagent (Pretreatment Solution: pH 7.5): | |
| --- | --- |
| HEPES | 50 mM |
| Nonion HS210 | 0.5% |
| KCl | 50 mM |
| NaCl | 100 mM |
| MgCl$_2$•6H$_2$O | 7.5 mM |
| NaN$_3$ | 0.1% |
| EDTA•2Na | 0.1 mM |
| PEP | 2 mM |
| ATP | 1 mM |
| PK | 1 KU/L |
| GK | 1 KU/L |
| ASOD | 2 KU/L |
| SMBTH | 1.5 mM |
| R2 Reagent (Color Development Solution: pH 7.5): | |
| HEPES | 50 mM |
| NaCl | 100 mM |
| NaN$_3$ | 0.1% |
| EDTA•2Na | 0.5 mM |
| HRP | 5 KU/L |
| PROD | 80 KU/L |
| HTIB | 6 mM |

Measurement Parameters in Example 3

| | |
| --- | --- |
| Analysis method | 2 Point end |
| Measurement points | 27 to 50 |
| Sample amount | 7 µL |
| R1 reagent | 240 µL |
| R2 reagent | 120 µL |
| Temperature | 37° C. |
| Measurement wavelength (main) | 750 nm |
| Calibration method | Straight-line method |
| Reference standard (1) | Saline (blank solution) |
| Reference standard (2) | 1,5-AG (50 µg/mL) saline solution |

The correlation coefficients between the resultant measured values and the measured values in Reference Example 1 are shown in Table 2.

Measurement Reagents in Example 4

HTIB (6 mM) in the R2 reagent (color development solution: pH 7.5) of Example 3 was replaced with HALPS (6 mM) to measure 1,5-AG in the 21 whole blood samples with the same parameters as those in Example 3. The correlation coefficient between the resultant measured values and the measured values in Reference Example 1 is shown in Table 2.

Measurement Reagents in Example 5

HTIB (6 mM) in the R2 reagent (color development solution: pH 7.5) of Example 3 was replaced with ADPS (6 mM) to measure 1,5-AG in 21 whole blood samples with the same parameters as those in Example 3. The correlation coefficient between the resultant measured values and the measured values in Reference Example 1 is shown in Table 2.

Measurement Reagents in Example 6

SMBTH(1.5 mM) in the R1 reagent (pretreatment solution: pH 7.5) of Example 3 and HTIB (6 mM) in the R2 reagent (color development solution: pH 7.5) thereof were replaced with 4AAP (1.5 mM) and ALPS (6 mM), respectively to measure 1,5-AG in 21 whole blood samples with the same parameters as those in Example 3. The correlation coefficient between the resultant measured values and the measured values in Reference Example 1 is shown in Table 2.

TABLE 2

Correlation Coefficient between Resultant Measured Values and Measured Values in Reference Example 1

| | Correlation Coefficient R |
| --- | --- |
| Example 3 | 0.978 |
| Example 4 | 0.959 |
| Example 5 | 0.996 |
| Example 6 | 0.923 |

The results in Table 2 show that the correlation coefficient between the measured values in Example 3, 4, 5, or 6 and the measured values in Reference Example 1 was 0.92 or more, indicating a high correlation. It is apparent that the measuring method of the present invention using these oxidative coupling-coloring chromogens provides accurate measurement results.

Example 7

Measurement of Glucose by Measuring Method of the Present Invention

Using the following R1 and R2 reagents, glucose in 3 whole blood samples was quantitatively measured with the following parameters employing Automated Analyzer Model 7150. The results are shown in Table 3.

| R1 Reagent (Pretreatment Solution: pH 7.5): | |
| --- | --- |
| HEPES | 50 mM |
| Nonion HS210 | 0.5% |
| KCl | 50 mM |
| NaCl | 100 mM |
| MgCl$_2$•6H$_2$O | 7.5 mM |
| NaN$_3$ | 0.1% |
| EDTA•2Na | 0.1 mM |
| Bovine serum albumin | 0.06% |
| ASOD | 5 KU/L |
| DAPS | 3 mM |
| R2 Reagent (Color Development Solution: pH 7.5): | |
| HEPES | 50 mM |
| NaCl | 100 mM |
| NaN$_3$ | 0.1% |
| EDTA•2Na | 0.5 mM |
| Potassium ferrocyanide | 0.1 mM |
| HRP | 5 KU/L |
| Glucose oxidase | 20 KU/L |
| SMBTH | 3 mM |

Measurement Parameters in Example 7

| | |
|---|---|
| Analysis method | 2 Point end |
| Measurement points | 24 to 50 |
| Sample amount | 2 μL |
| R1 reagent | 280 μL |
| R2 reagent | 140 μL |
| Temperature | 37° C. |
| Measurement wavelength (main) | 750 nm |
| Calibration method | Straight-line method |
| Reference standard (1) | Saline (blank solution) |
| Reference standard (2) | Glucose (200 mg/dL) aqueous solution |

Reference Example 3

Measurement of Glucose in Serum by Ordinary Method

Using GL-5 Kainos (from Kainos Laboratories, Inc.) as a reagent for measuring glucose in serum and Automated Analyzer Model 7150, the glucose concentration in the serum collected simultaneously with the blood measured in Example 7 was measured; the results obtained are shown in Table 3.

TABLE 3

Measured Value of Glucose (Unit: mg/dL)

| | Reference Example 3 (Plasma) | Example 7 (Whole Blood) |
|---|---|---|
| Whole Blood Sample 1 | 106.0 | 99.5 |
| Whole Blood Sample 2 | 105.0 | 106.2 |
| Whole Blood Sample 3 | 86.3 | 84.4 |

The results in Table 3 show that the measured values in Reference Example 3, which are the measured values of the glucose concentration in plasma, were in good agreement with the measured values in Example 7, which are the measured values by the method of the present invention using whole blood. It is apparent that glucose can be measured using whole blood by the measuring method of the present invention.

Reference Example 4

Relation Between Hemolyzing Agent Concentration in R1 Reagent and Hemolysis

To examine the relation between the hemolyzing agent concentration in an R1 reagent and the degree of hemolysis, saline, which is a solution isotonic with blood cells, was used as the R1 reagent and a nonionic surfactant, HS210, was used as the hemolyzing agent. Hemolysis does not occur when whole blood is mixed with saline since saline is isotonic with blood cells; thus, light transmission is hindered by the presence of cells, which increases the absorbance (ABS; OD×10,000) of 39,000 or more at the 25th point (at 5 minutes after mixing a whole blood specimen with the following R1 reagent) when the absorbance was measured with the following parameters using Automated Analyzer Model 7150. Such high absorbance at the 25th point may cause wide variation because the measurement is made outside the measurement range of an absorption spectrometer and thus, it does not allow for the accurate measurement of absorption for color developed in the second reaction as a detection reaction following the first reaction.

In contrast, the use of purified water in place of saline causes hemolysis of blood cells because of an osmotic pressure change when mixing purified water with whole blood. As a result, the absorbance at the 25th point decreases to one-tenth of the absorbance of the mixture using saline.

Absorbance (ABS) at the 25th point (at 5 minutes after mixing a whole blood specimen with each of R1 reagents (salines containing various concentrations of HS210)) was measured with the following parameters using Automated Analyzer Model 7150. The results are shown in Table 4.

In addition, 14 μL of the whole blood sample and 560 μL of each R1 reagent were mixed in a micro test tube and allowed to stand at room temperature for 1 hour, which was then observed to confirm the presence of sedimentation of blood cells. The results are shown in Table 4.

Measurement Parameters in Reference Example 4

| | |
|---|---|
| Measurement points | 25 |
| Sample amount | 7 μL |
| R1 reagent | 280 μL |
| R2 reagent | 0 μL |
| Temperature | 37° C. |
| Measurement wavelength (main) | 600 nm |

TABLE 4

Relation between Hemolyzing Agent Concentration in R1 Reagent and Hemolysis

| HS210 Concentration (%) in R1 Reagent | ABS at 25 Points (OD × 10,000) | Presence of Blood Cell Sedimentation |
|---|---|---|
| 0 | 39713 | Yes |
| 0.01 | 39772 | Yes |
| 0.03 | 8466 | Yes |
| 0.05 | 2230 | No |
| 0.1 | 1962 | No |
| 0.3 | 1768 | No |
| 0.5 | 1846 | No |
| 1.0 | 1403 | No |
| 2.0 | 1590 | No |
| Reference: Purified Water Used as R1 Reagent. | 2602 | No |

The results in Table 4 show that the samples were hemolyzed in the case of the HS210 concentration in the R1 reagent being 0.05% or more since ABS at 600 nm was remarkably decreased and no blood cell sedimentation occurred, which is the same results as the test with purified water. The optimal concentration of hemolyzing agents for hemolysis depends on the type of hemolyzing agents, the composition of the R1 reagent, and the mixing ratio of a sample and the R1 reagent. Thus, it is advisable to determine their optimal concentrations respectively.

Example 8

Method for Converting Measured Value of 1,5-AG Obtained Using Whole Blood Sample to 1,5-AG Concentration in Plasma (1)

1,5-AG was measured using "1,5-AG Kit for Animals" (from Nippon Kayaku Co., Ltd.) to study a method for correcting the measured value of 1,5-AG in whole blood to the 1,5-AG concentration in plasma.

Using blood-collecting vessels containing EDTA, 2 mL each of whole blood samples of 7 subjects were collected, and each sample was divided into a sample for whole blood measurement and a sample for plasma measurement. In addition, the hematocrit value was measured using a portion of the sample for whole blood measurement.

One hundred microliters of purified water was added to 25 μL of each sample, which was then strongly stirred to obtain the quintuple diluted hemolysate. The whole blood specimen sample was checked its light transmission for confirmation of complete hemolysis.

One hundred microliters of a standard solution containing no 1,5-AG (purified water), a standard solution having a 1,5-AG concentration of 5 μg/mL, or each of the above quintuple diluted samples was applied to the pretreatment column of the "1,5-AG Kit for Animals" conditioned with purified water in advance, and each eluate was collected in separate test tubes. Next, 300 μL of purified water was added to each pretreatment column to elute 1,5-AG. The operation of adding 300 μL of purified water was further repeated 2 times to completely recover 1,5-AG. The total volume of the solution pooled in each test tube reached 1.0 mL.

The coloring reagent (100 μL) and an enzyme reagent (100 μL) of the "1,5-AG Kit for Animals" were added to each test tube and stirred, followed by immersion in a thermostat bath at 20° C. for reaction for 30 minutes. After reaction, 100 μL of the reaction-stopping solution of the "1,5-AG Kit for Animals" was added to the test tube and stirred to stop the enzyme reaction.

A microcell having an optical path length of 1 cm was used to measure the absorbance of each reaction solution at 727 nm using purified water as a reference. A two-point calibration curve was made from the absorbances of the standard solution containing no 1,5-AG and the 5 μg/mL standard solution, and it was used to determine the 1,5-AG concentration in each sample from the absorbance of each reaction solution. The results are shown in Table 5. The standard solutions and the samples were each subjected to measurement twice, and the average values thereof are shown.

Then, the ratios of the measured values obtained by dividing the measured values (a) of 1,5-AG in the whole blood samples by the measured values (b) of 1,5-AG in plasma samples, that is, the recovery rates for whole blood measurement (a/b) were determined and are shown in Table 5 and the average value of the recovery rates thereof was calculated.

For this Example, the average value of the recovery rates is 0.85, showing that the measured values of 1,5-AG in the whole blood samples are of the order of 15% lower than the measured values of 1,5-AG in the plasma samples.

Accordingly, the converted values of the 1,5-AG measured value determined by dividing the measured values of 1,5-AG in the whole blood samples by the average value of the above ratios (a/b) are shown in Table 5. These converted values were in good agreement with the 1,5-AG concentrations in plasma samples.

The results of this Example showed no correlation between the hematocrit values and the above ratios (a/b) (correlation coefficient R: 0.067). Thus, the hematocrit value cannot be directly used for correction.

In the test of this Example, an analysis was carried out based on the results from only 7 cases of samples. It will be apparent that more accurate converted values can be obtained if the same analysis is performed using many samples.

TABLE 5

Measured Value of 1,5-AG Obtained by Colum Method

| Sample | Measured Value of 1,5-AG (μg/mL) | | Correction by a/b Average Value | | Hematocrit (%) |
|---|---|---|---|---|---|
| | Whole Blood (a) | Plasma (b) | Whole Blood Measurement (a/b) | Converted Value (μg/mL) | |
| 1 | 7.4 | 8.7 | 0.85 | 8.7 | 33 |
| 2 | 12.6 | 14.9 | 0.85 | 14.8 | 38 |
| 3 | 11.6 | 12.8 | 0.91 | 13.6 | 40 |
| 4 | 20.8 | 24.7 | 0.84 | 24.5 | 38 |
| 5 | 19.4 | 22.3 | 0.87 | 22.8 | 45 |
| 6 | 23.8 | 28.0 | 0.85 | 28.0 | 41 |
| 7 | 24.1 | 29.8 | 0.81 | 28.4 | 40 |
| Average Value | 17.1 | 20.0 | 0.85 | 20.1 | 39 |

Example 9

Method for Converting Measured Value of 1,5-AG Obtained Using Whole Blood Sample to 1,5-AG Concentration in Plasma (2)

A method was studied for converting the values of 1,5-AG measured in a whole blood sample to the 1,5-AG concentration in plasma by using Automated Analyzer Model 7150, which is conventionally used for biochemical testing.

Using blood-collecting vessels containing EDTA, 2 mL each of whole blood samples from 21 subjects were collected, and each sample was divided into the sample for whole blood measurement and the sample for plasma measurement.

The concentration of 1,5-AG in the samples for plasma measurement was determined under the method of Reference Example 1 while using the plasma obtained by centrifuging the whole blood sample. The resultant measured values are shown in Table 6.

The concentration of 1,5-AG in the samples for whole blood measurement was determined based on the following parameters while using the R1 and R2 reagents prepared in the following compositions. The resultant measured values are shown Table 6.

| R1 Reagent (Pretreatment Solution: pH 7.5): | |
|---|---|
| HEPES | 50 mM |
| Nonion HS210 | 0.5% |
| KCl | 50 mM |
| NaCl | 100 mM |
| $MgCl_2 \cdot 6H_2O$ | 7.5 mM |
| $NaN_3$ | 0.1% |
| EDTA·2Na | 0.1 mM |
| PEP | 2 mM |
| ATP | 1 mM |
| PK | 1 KU/L |
| GK | 1 KU/L |
| ASOD | 2 KU/L |
| SMBTH | 1.5 mM |
| R2 Reagent (Color Development Solution: pH 7.5): | |
| HEPES | 50 mM |
| NaCl | 100 mM |
| $NaN_3$ | 0.1% |
| EDTA·2Na | 0.5 mM |
| HRP | 5 KU/L |
| PROD | 80 KU/L |

-continued

| | |
|---|---|
| TOOS | 6 mM |

Measurement Parameters:

| | |
|---|---|
| Analysis method | 2 Point end |
| Measurement points | 27 to 50 |
| Sample amount | 7 μL |
| R1 reagent | 280 μL |
| R2 reagent | 140 μL |
| Temperature | 37° C. |
| Measurement wavelength (main) | 600 nm |
| Calibration method | Straight-line method |
| Reference standard (1) | Saline (blank solution) |
| Reference standard (2) | 1,5-AG (50 μg/mL) saline solution |

Figure 3:
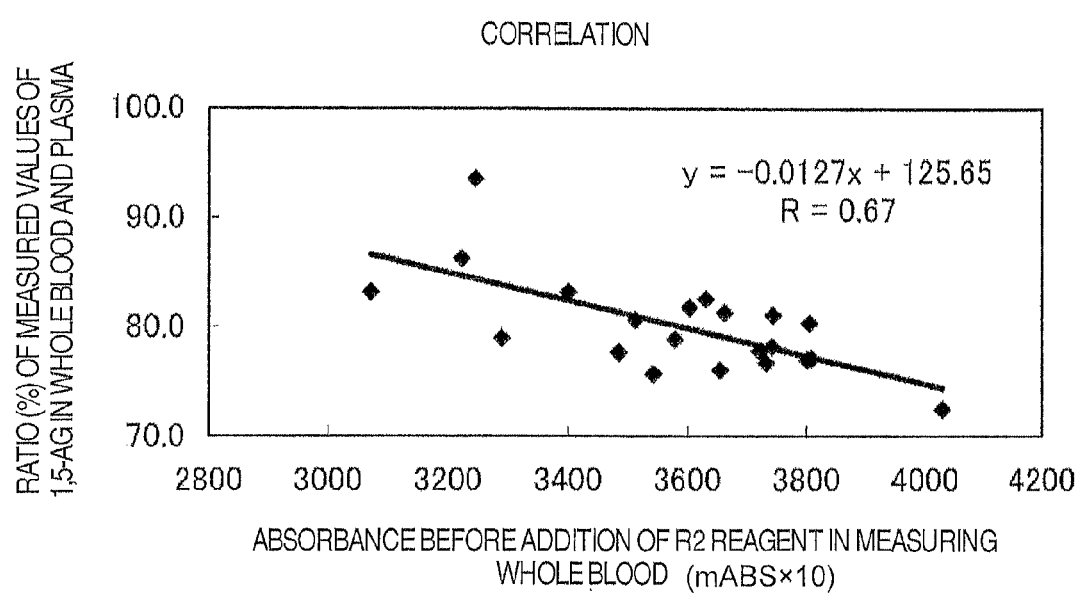
FIG. 3 is a graph showing the correlation between the recovery rate for whole blood measurement (a/b) and absorbance at the 24th point.

Recovery rates for whole blood measurement (a/b), which are the ratios between the measured values of 1,5-AG in the whole blood samples (a) and the measured values of 1,5-AG in the plasma samples (b), were determined to analyze a value related to hemoglobin, which correlates with the recovery rates. As a result, as shown in FIG. 3, the absorbances (mABS×10) at the 24th point in measuring the whole blood samples, that is, the absorbances before addition of the R2 reagent, were found to show good correlation with the recovery rates for whole blood measurement (a/b) (correlation coefficient R: 0.67). From this, the following correlation formula as a linear approximation formula is derived:

Recovery rate for whole blood measurement (a/b; %)=−0.0127×(Absorbance at the 24th point; mABS×10)+125.65.

This can be used to convert the measured value of 1,5-AG in a whole blood sample to the 1,5-AG concentration in plasma by dividing the measured value by the recovery rate for whole blood measurement (a/b) calculated from absorbance before addition of the R2 reagent.

Absorbances at the 24th point in measuring 1,5-AG in the whole blood samples are shown in Table 6. The converted value determined by dividing the measured value of 1,5-AG in each whole blood sample by the recovery rate of whole blood measurement (a/b) calculated using the above correlation formula and each of these absorbances is shown in Table 6.

Figure 4:
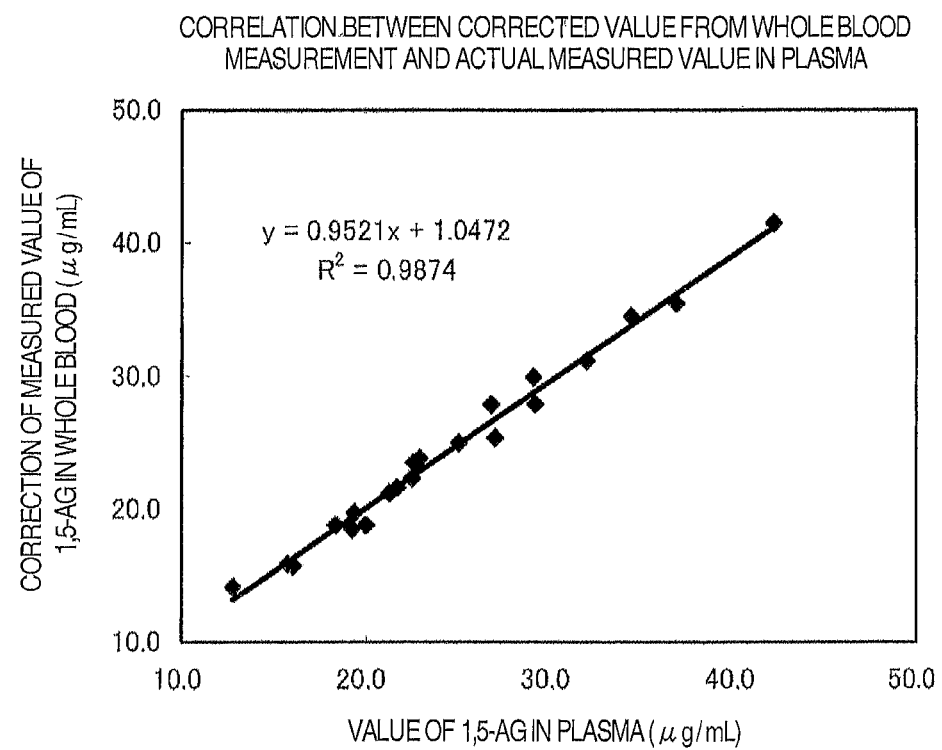
FIG. 4 is a graph showing the correlation between the converted value in plasma determined from a whole blood measurement value and the actual measured value in plasma.

As shown in FIG. 4, these converted values were extremely close to the measured values of 1,5-AG in the corresponding plasma samples (correlation formula: converted value=0.9521×(measured value in plasma)+1.0472) and had high correlation therewith (correlation coefficient R=0.9937). It is apparent that the conversion method of the present invention is useful.

TABLE 6

Measured Value of 1,5-AG Obtained Using General-Purpose Measuring Machine for Biochemical Test

| Sample | Measured Value of 1,5-AG (μg/mL) Whole Blood (a) | Measured Value of 1,5-AG (μg/mL) Plasma (b) | Recovery Rate for Whole Blood Measurement (a/b: %) | Absorbance before Addition of R2 in Measuring Whole Blood (mABS) | Converted Value of 1,5-AG (μg/mL) |
|---|---|---|---|---|---|
| 1 | 15.1 | 18.4 | 81.8 | 3604 | 18.8 |
| 2 | 19.3 | 25.0 | 77.1 | 3808 | 24.9 |
| 3 | 18.7 | 22.6 | 82.6 | 3632 | 23.5 |
| 4 | 28.1 | 36.9 | 76.0 | 3655 | 35.4 |
| 5 | 13.1 | 15.8 | 83.2 | 3401 | 15.9 |
| 6 | 21.5 | 26.8 | 80.3 | 3805 | 27.8 |
| 7 | 23.2 | 32.0 | 72.5 | 4029 | 31.1 |

TABLE 6-continued

Measured Value of 1,5-AG Obtained Using General-Purpose Measuring Machine for Biochemical Test

| Sample | Measured Value of 1,5-AG (μg/mL) Whole Blood (a) | Measured Value of 1,5-AG (μg/mL) Plasma (b) | Recovery Rate for Whole Blood Measurement (a/b: %) | Absorbance before Addition of R2 in Measuring Whole Blood (mABS) | Converted Value of 1,5-AG (μg/mL) |
|---|---|---|---|---|---|
| 8 | 16.7 | 19.4 | 86.3 | 3223 | 19.8 |
| 9 | 23.7 | 29.1 | 81.3 | 3663 | 29.9 |
| 10 | 17.5 | 21.7 | 80.7 | 3513 | 21.6 |
| 11 | 26.9 | 34.4 | 78.3 | 3742 | 34.5 |
| 12 | 33.2 | 42.1 | 78.9 | 3580 | 41.4 |
| 13 | 12.0 | 12.8 | 93.6 | 3246 | 14.2 |
| 14 | 20.4 | 27.0 | 75.7 | 3544 | 25.3 |
| 15 | 15.8 | 20.0 | 79.0 | 3290 | 18.8 |
| 16 | 22.7 | 29.2 | 77.7 | 3485 | 27.9 |
| 17 | 16.4 | 21.3 | 77.0 | 3802 | 21.2 |
| 18 | 18.6 | 22.9 | 81.1 | 3744 | 23.8 |
| 19 | 16.1 | 19.3 | 83.2 | 3071 | 18.5 |
| 20 | 12.4 | 16.1 | 76.7 | 3733 | 15.8 |
| 21 | 17.5 | 22.5 | 77.8 | 3722 | 22.3 |

Similarly, an analysis was carried out using a power approximation formula and a logarithmic approximation formula. The correlation formulas are: Recovery rate for whole blood measurement (a/b; %)=6942.4×(Absorbance at the 24th point; mABS×10)$^{0.5456}$ and Recovery rate for whole blood measurement (a/b; %)=−44.558×ln (Absorbance at the 24th point; mABS×10)+444.63 (ln: natural logarithm), respectively. The converted values determined from the measured values in whole blood using these correlation formulas were extremely close to the measured values of 1,5-AG in the corresponding plasma samples and showed high correlation therewith. The correlation formulas and correlation coefficients were: Converted value=0.9542×(Measured value in plasma)+1.0403 and Correlation coefficient 0.9936 for the power approximation formula and Converted value=0.9536×(Measured value in plasma)+1.0362 and Correlation coefficient=0.9937 for the logarithmic approximation formula.

INDUSTRIAL APPLICABILITY

According to the measuring method of the present invention, the quantity of an analyte, 1,5-anhydroglucitol for example, in the blood can be determined by using whole blood without separating blood cells and by detecting hydrogen peroxide generated by the reaction of an oxidase with the analyte, and therefore, the analyte can be measured simply, rapidly and accurately at places such as a patient's home, a private clinic having no blood cell separation device, and a patient's bedside.

In addition, the measured value of the analyte measured according to the method of the present invention using a whole blood sample is converted to the concentration thereof in serum or plasma by the conversion method of the present invention to easily compare with a previous test value or a reference value, which was measured or determined using serum or plasma.

The invention claimed is:
1. A method for measuring a concentration of 1,5-anhydroglucitol in a whole blood sample, the method comprising the steps of:
(a) hemolzying the whole blood sample and enzymatically eliminating glucose;

(b) reacting the 1,5-anhydroglucitol in the whole blood sample with an oxidase;
(c) detecting hydrogen peroxide generated by the reaction between the 1,5-anhydroglucitol and the oxidase by administering a chromogen;
(d) measuring a color intensity of the whole blood sample at a wavelength from 580 nm to 900 nm;
wherein step (a) must be followed by step (b).

2. The method according to claim 1, wherein the step of hemolyzing the whole blood sample comprises mixing the whole blood sample with a hemolyzing agent.

3. The method according to claim 2, wherein the hemolyzing agent is a surfactant.

4. The method according to claim 1, wherein the step of detecting the hydrogen peroxide comprises using peroxidase.

5. The method according to claim 1, wherein the chromogen is an oxidative coupling-coloring chromogen.

6. The method according to claim 5, wherein the oxidative coupling-coloring chromogen is a chromogen comprising
   4 aminoantipyrine, 3-methyl-2-benzothiazolinone hydrazone or 2-hydrazono-2,3-dihydro-3-methyl-6-benzothiazolesulfonic acid; and
   N-ethyl-N-sulfopropyl-3,5-dimethoxyaniline, 3-hydroxy-2,4,6-triiodobenzoic acid, N-ethyl-N-(2-hydroxy-3-sulfopropyl)-3-methoxyaniline, N-sulfopropylaniline, N-ethyl-N-sulfopropyl-m-anisidine, or N-ethyl-N-sulfopropylaniline.

7. The method according to claim 1, wherein the oxidase is pyranose oxidase or L-sorbose oxidase.

8. The method according to claim 1, wherein the color intensity of the dye is determined while hydrogen peroxide is generated by reacting 1,5-anhydroglucitol with the oxidase.

* * * * *